United States Patent
Subramaniam et al.

(10) Patent No.: US 6,924,407 B2
(45) Date of Patent: Aug. 2, 2005

(54) PRESSURE-TUNED SOLID CATALYZED HETEROGENEOUS CHEMICAL REACTIONS

(75) Inventors: Bala Subramaniam, Lawrence, KS (US); Christopher James Lyon, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 09/940,015

(22) Filed: Aug. 27, 2001

(65) Prior Publication Data

US 2003/0073876 A1 Apr. 17, 2003

(51) Int. Cl.⁷ ............... C07C 2/56; C07C 5/22; B01J 20/00
(52) U.S. Cl. ............ 585/952; 585/709; 585/470; 502/20
(58) Field of Search ............... 585/952, 470, 585/709; 502/20

(56) References Cited

U.S. PATENT DOCUMENTS 4,056,578 A * 11/1977 McClure et al. ............ 585/730
5,491,278 A * 2/1996 Angstadt et al. ............ 585/731
5,907,075 A * 5/1999 Subramaniam et al. ..... 585/721

* cited by examiner

Primary Examiner—Thuan D Dang
(74) Attorney, Agent, or Firm—Hovey Williams LLP (57) ABSTRACT

Improved methods for conducting solid acid-catalyzed, near- or supercritical heterogeneous chemical reactions (e.g., alkylation reactions) are provided which give enhanced product yields and permit longer processing runs. The preferred reactions of the invention are carried out in the presence of a solid macroporous catalyst having a surface area of from about 50–400 $m^2/g$ and a pore size of from about 70–150 Å. Product selectivity is enhanced by pressure-tuning of the reaction to promote production and separation of desired reaction products. In continuous processing, the chemical reaction may be interrupted before significant catalyst deactivation, followed by increasing reactor pressure and/or reducing reactor temperature to remove the accumulating coke; when the catalyst is regenerated, the original reaction conditions and reactant introduction may be resumed.

21 Claims, 10 Drawing Sheets

Figure 1

Steady alkylation activity on SAC-13 catalyst. 80 bar, 368 K, 0.05 $h^{-1}$ OSV, I/O=5, $CO_2$= 70 mole %.

Figure 2

Pressure tuning effect on alkylation activity. 368 K, I/O=5, 0.05 h$^{-1}$

Figure 3

Liquid (26 bar) vs. supercritical phase alkylation (95 bar, 70 mole% $CO_2$) on SAC-13. 368 K, 0.05 $h^{-1}$ OSV, I/O=10.

Figure 4

Supported (SAC-13) vs. unsupported Nafion® catalysts. 80 bar, 368 K, 0.05 h$^{-1}$ OSV, I/O=5, 70 mole% $CO_2$.

Figure 5

Effect of reactor configuration. 97 bar, 368 K, 0.05 h$^{-1}$ OSV, I/O=10

PRESSURE-TUNED SOLID CATALYZED HETEROGENEOUS CHEMICAL REACTIONS

BACKGROUND OF THE INVENTION

1. Field of the Invention

The present invention is broadly concerned with improved methods of conducting solid acid-catalyzed, near- or supercritical heterogeneous chemical reactions such as alkylation reactions in order to improve the efficiency thereof and the tendency for the reactions to be prematurely terminated owing to coke laydown on the catalyst. More particularly, the invention is concerned with such methods wherein reaction product selectivity is enhanced by pressure-tuning the reaction together with use of particular types of solid acid catalysts having relatively narrow surface area and pore size characteristics. The invention also provides a way of substantially continuously maintaining a chemical reaction by appropriately timed catalyst regeneration cycles during the course of the reaction.

2. Description of the Prior Art

Conventional isoparaffin/olefin alkylation processes, practiced since the 1930's, convert light refinery gases to high octane number gasoline range hydrocarbons (e.g. trimethylpentane) using liquid sulfuric or hydrofluoric acid catalysts. These processes typically convert refinery gasses such as $C_4$–$C_5$ isoparaffins into more valuable branched chain gasoline-range $C_7$–$C_9$ alkylate compounds. Particularly valuable alkylates are trimethylpentanes (TMPs) and 2,2-dimethylbutane (neohexane) which are used as high-octane blending components for aviation and civilian gasolines. It is estimated that about 13% of the U.S. gasoline pool is made up of alkylates.

However, economic and environmental concerns associated with liquid acid catalyst handling, regeneration, and disposal, have spurred the search for an alternative process. Since the early 1970's, the use of solid acid catalysts as a replacement has been investigated (Corma, et al., *Catal. Rev.-Sci. Eng.*, 35 (1993) 483), but in many instances the results have been disappointing. The reason is that solid acid catalysts tend to deactivate rapidly with time due to buildup of heavy hydrocarbons on the catalyst surface. The deactivating pathway is believed to suppress the hydride transfer mechanism, which is dependant on the acid site density (Pater, J., et al. *Ind. Eng. Chem. Res.* 38 (1999) 3822). Among the most common solid acids to be investigated are zeolites, sulfated zirconia, and aluminum chloride. (Corma, et al., *Catal. Rev.-Sci. Eng.*, 35 (1993) 483; Rao, P., et al., *Prep.-Div. Pet. Chem. ACS,* 41 (1996) 685; and Weitkamp, J. and Traa, Y. *Catal. Today,* 49 (1999) 93).

U.S. Pat. No. 5,907,075 represents a significant advance in the art and describes improved solid acid catalyst supercritical alkylation processes which ameliorate the catalyst coking problem. The '075 patent teaches that use of a co-solvent or diluent such as $CO_2$ together with supercritical reaction conditions have the effect of lessening the coke laydown difficulty. However, after a certain period of reaction time, the catalyst will nevertheless become deactivated because of coke buildup, and a "breakthrough" will occur, meaning that the production of desired reaction product will decline usually in a precipitous fashion.

The liquid-like densities yet significantly better-than-liquid diffusivities of supercritical (sc) reaction media have been shown to be more desirable than either liquid or gas phases to mitigate catalyst deactivation by coking (Subramaniam, B., *Appl. Catal.* 212 (2001) 199). Gas phase isobutane/butene alkylation is not practical because of the low volatility of the primary products ($C_8$'s), which undergo subsequent reaction such as oligomerization on the catalyst resulting in rapid catalyst deactivation. Operation in a liquid phase provides the maximum solubility for removing adsorbed heavy hydrocarbons. However, the pore diffusion rate in a liquid is much lower than that in a gas phase. This increases the likelihood of readsorption and further reaction of the solvated molecules in the pore.

It has been shown in the literature that isobutane ($P_c$=36.5 bar, $T_c$=408 K) /butene ($P_C$=40.2 bar, $T_C$=420 K) alkylation on solid acid catalysts at supercritical temperatures suffers from increased butene oligomerization and cracking reactions at these temperatures, increasing the catalyst deactivation potential (Fan, L., et al. *Ind. Eng. Chem. Res.*, 36 (1997) 1458; Funamoto, G., et al. *Res. Chem. Intermed.*, 24 (1998) 449; and Gayraud, P., et al. *Catal. Today,* 63 (2000) 223). Lower temperatures tend to favor the alkylation reaction. Supercritical operation at 95° C. can be facilitated by diluting the isoparaffin/olefin feed with suitable amounts of a low $T_c$ inert solvent such as $CO_2$ ($P_c$=73.8 bar, $T_c$=304 K), and has been shown to give rise to steady alkylation activity on USY and beta zeolites (Clark, M., et al., *Ind. Eng. Chem. Res.*, 37 (1998) 1243). However, the alkylate yields are very low (<10%) on these catalysts, attributed to severe pore diffusion limitations on these catalysts.

Nafion® is a perfluorinated polymer with sulfonic acid groups grafted to side chains, yielding acidity similar to that of sulfuric acid (Fărcaşiu, D. et al. *J. Am. Chem. Soc.*, 119 (1997) 11826). Nafion® has not been extensively studied as a catalyst for isoparaffin alkylation, although it has shown good activity for a number of acid catalyzed reactions (Olah G., et al. *Synthesis* (1978) 672; Chaudhuri, B., et al al., *Ind. Eng. Chem. Res.*, 30 (1991) 227; Yamato, T., et al., *J. Org. Chem.*, 56 (1991) 2089; and Sun, Q., et al. *Ind. Eng. Chem. Res.*, 36 (1997) 5541). Nafion® is available in both unsupported and supported forms. In the supported form, the polymer is impregnated on high surface area silica supports, which has been shown to improve accessibility to acid sites (Harmer, M., et al. *Chem. Comm.*, (1997) 1803; and Sun, Q., et al. *Ind. Eng. Chem. Res.*, 36 (1997) 5541).

Rørvik, et al. studied unsupported Nafion® for isobutane/ 1-butene alkylation in a stirred liquid phase batch reactor (Rørvik, T., et al. *Catal. Lett.*, 33 (1995) 127). The production of trimethylpentanes (the most desirable alkylate product) was shown to cease within 30 minutes of operation. More recently, silica-supported Nafion® was used to catalyze the same reaction (Botella, P., et al. *J. Catal.*, 185 (1999) 371). Once again, rapid deactivation with respect to trimethylpentane formation was observed. It was hypothesized that the strongest acid sites—the most active for alkylation—are also the first to be poisoned.

SUMMARY OF THE INVENTION

The present invention overcomes the problems outlined above and provides improved methods for conducting acid-catalyzed heterogeneous chemical reactions using a reactant mixture comprising one or more heterogeneous reactant(s) (e.g., alkylation, acylation, isomerization, aromatic disproportionation, alcohol synthesis, and Fischer-Tropsch reactions) under near- or supercritical conditions, in order to avoid, or at least substantially control, problems heretofore encountered in such reactions owing to coke laydown. Broadly speaking, in one aspect of the invention, it has been found that use of particular types of macroporous solid catalysts significantly delays the onset of catalyst deactivation owing to coke laydown under supercritical reaction conditions. In another aspect, it has been discovered that heterogeneous reactions of this type may be pressure-tuned to maximize selectivity of desired end products, while also permitting regeneration of the solid catalyst prior to significant catalyst deactivation; this permits use of a dual reactor system wherein the respective reactors may be used in an alternate fashion, cycling between reaction duty and catalyst regeneration.

In more detail, in preferred forms of the invention, the catalyst used in heterogeneous near- or supercritical chemical reactions should have a BET surface area of from about 50–400 m$^2$/g, and more preferably from about 10–300 m$^2$/g. and most preferably about 200 m$^2$/g. The catalyst should also have an average pore size on the order of from about 70–150 Å, more preferably from about 80–120 Å, and most preferably about 100 Å. Although a number of solid catalysts can be used to good effect, supported perfluorinated polymer catalysts having sulfonic acid groups coupled thereto are preferred, such as the known Nafion® catalysts. This preferred catalyst has the following characteristics: SiO$_2$ support—87% wt % SiO$_2$ (CAS 112945-52-5), 13% tetrafluoroethylene-perfluoro-3,6-dioxaq-4-methyl-7-octenesulfonic acid copolymer (CAS 31175-20-9), BET surface area ~200 m$^2$/g, acid capacity 0.14 meqH/G; Nafion®—a solid superacid catalyst ion exchange polymer (exhibiting an acid strength comparable to that of H$_2$SO$_4$) including a perfluorocarbon backbone with sulfonic acid side groups. Other suitable catalyst resins would include Amberlyst® (sulfonated polystyrene divinyl benzene resin), Ionac® (sulfonated polystyrene divinyl benzene resin) and Deloxan® (sulfonated polysolixane resin), where such resins would be used with a solid support such as SiO$_2$.

Reaction conditions should typically be in the neighborhood of from about 0.9–1.3T$_c$ of the reactant mixture (i.e., the reactant(s) fed to the reactor), and more preferably from about 1.01–1.2 T$_c$. Similarly, pressure conditions are advantageously maintained at a level of from about 0.9–2.5 P$_c$ of the reactant mixture, more preferably from about 1.01–1.2 P$_c$ thereof.

Where continuous heterogeneous reactions are contemplated which include a co-solvent or diluent, improvements are obtained by periodic catalyst regeneration cycles during the course of a substantially steady state reaction. Thus, the solid acid catalysts may be regenerated by terminating introduction of at least one of the reactant(s) to the reactor prior to a time when the solid catalyst is significantly deactivated owing to coke laydown. Thereupon, the pressure within the reactor is elevated and/or the temperature therein is lowered to remove at least a portion of any coke on the catalyst. When this is accomplished, the chemical reaction may be resumed by reestablishing substantially steady state conditions within the reactor and again commencing full introduction of reactant(s) into the reactor.

In more detail, it is desired that the catalyst regeneration be carried out before the rate of production of a desired reaction product falls by a factor of 20% (more preferably 35%), as compared with the steady state reaction product production rate before the catalyst regeneration step. In practice, the appropriate time to begin the catalyst regeneration can be readily determined by ascertaining when the "breakthrough" for the reaction occurs, that is when the characteristic rapid decline in production of the desired reaction product(s) is observed. It has been found the continuity of heterogeneous reactions may be maintained almost indefinitely by proper cycling of a reactor between reaction and catalyst regeneration stages. Generally speaking, the higher pressure catalyst regeneration step is carried out at pressures which are elevated by at least about 40%, as compared with the pressure within the reactor during the normal chemical reaction. In many instances, the higher regeneration pressures are obtained by introduction of additional high pressure CO$_2$ or other co-solvent or diluent; CO$_2$ may be used alone or mixed with other solvents such as ethane or isobutane to obtain a better removal of coke from the catalyst (in this context, "coke" refers to extractable carbonaceous deposits left on the surface of the catalyst). Where the temperature is lowered during catalyst regeneration, care should be taken to insure that the reactor temperature remains above the Tc of the co-solvent or diluent. It will also be appreciated that in some instances the coke derived from catalyst regeneration may itself be a valuable or desired product, and that the coke may be conventionally recovered in such cases.

On a fundamental level, the invention utilizes the pressure-tunable properties of near- or supercritical reaction mixtures for the simultaneous reaction and product separation during heterogeneous catalytic reactions. The physical properties such as density, diffusivity, heat capacity, etc. of a near- or supercritical reaction mixture are very sensitive to small changes in pressure. For a reaction being conducted in a single phase, the products often have different critical properties and/or solubilities as compared with the starting reactants. As a consequence, some of the products formed in the catalyst pores may dissolve in the near- or supercritical reaction mixture, while the formation of heavier products can cause a second liquid or solid phase to form. By carefully choosing suitable operating conditions which cause selected products to be removed from the catalyst while retaining the heavier products inside the catalyst pores, certain products can be preferentially deposited in the catalyst pores, resulting in product separation. In effect, the catalyst pores act as a reservoir for selected products. At a later time when the pores can no longer hold the heavier products without the catalyst undergoing significant deactivation, the operating conditions in the reactor are adjusted to regenerate and clean the catalyst pores so that the heavier products are dissolved and extracted out of the catalyst pores. Once the pores are clean (i.e., the catalyst is regenerated) the initial operating steady state conditions may be reestablished and the simultaneous reaction/in situ product separation step is repeated. These chemical reaction/catalyst regeneration cycles can be repeated continuously.

The invention finds particular utility in alkylation reactions wherein reactants include an isoparaffin, an olefin, and a molar excess of an inert co-solvent or diluent. Preferably, the isoparaffin is selected from the group consisting of C$_4$–C$_{10}$ isoparaffins, and said olefin selected from the group consisting of the C$_2$–C$_{10}$ olefins. Reaction conditions for the alkylation reactions typically are: pressure from about 500–3,000 psi, more preferably from about 1,000–2,500 psi; temperature from about 325–450K, more preferably from about 350–400K. The peroxide content of the reaction mixture should be no more than about 200 ppm, preferably below about 100 ppm. Furthermore, the co-solvent or diluent having a critical temperature less than the critical temperatures of each of the isoparaffin and olefin. The preferred co-solvent or diluent is selected from the group consisting of carbon dioxide, methane, ethane, hydrogen, and mixtures thereof. Finally, the reaction mixture should have a fluid density of from about 0.05–0.65 g/cc. Generally speaking, the reaction conditions useful for alkylation reactions are those set forth in U.S. Pat. No. 5,907,075 incorporated by reference herein.

It has been found that butene conversion and production of desirable $C_8$ alkylates are significantly increased in the present invention. For example, in prior processes butene conversions of 10–15% and 5–10% yields of $C_8$ alkylates are common. However, with the present invention 75–80% butene conversions and 25–30% $C_8$ alkylate yields are readily attainable.

DETAILED DESCRIPTION OF THE PREFERRED EMBODIMENTS

The following examples set forth preferred techniques for carrying out the heterogeneous, solid-catalyzed reaction methods in accordance with the invention. It is to be understood, however, that these examples are provided by way of illustration only, and nothing therein should be considered as a limitation upon the overall scope of the invention.

EXAMPLE 1

In this example, a series of supercritical condition alkylation reactions of butene and isoparaffin with a molar excess of carbon dioxide were carried out using a preferred catalyst in order to demonstrate temporal and selectivity profiles for the reactions.

Figure 1:
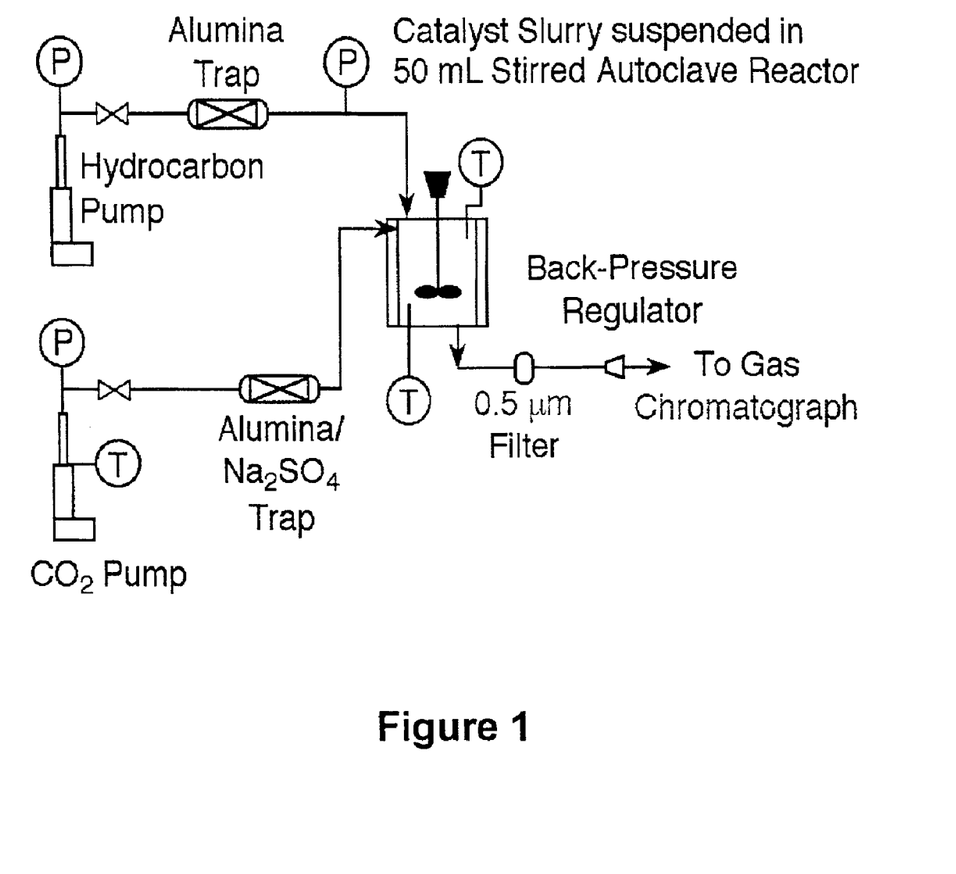
FIG. 1 is a schematic representation of the reaction equipment employed in carrying out alkylation methods in accordance with the invention.

The reactor schematic is shown in FIG. 1. Continuous stirred tank reactor (CSTR) experiments were conducted in a 50 mL Microclave from Autoclave Engineers, rated to 344 bar and 616 K. Catalyst particles were suspended in the reaction mixture by an impeller operating at 1200 RPM. Fixed-bed reactor experiments were conducted in a 1" I.D. stainless steel tubular reactor from Autoclave Engineers, rated to 1110 bar at 700 K. The catalyst bed was supported on both ends with glass wool (Alltech) and stainless steel mesh screens, which were confirmed to be inert under reaction conditions.

The catalysts investigated were characterized before and after use. Unsupported Nafion® polymer beads and 13% Nafion® on silica (SAC-13) catalysts were furnished by DuPont and Engelhard Corp., respectively. Surface area (SA) and pore volume (PV) measurements were done using a Micromeretics Gemini instrument, employing nitrogen physisorption. The acid site concentration was measured by a NaCl ion-exchange/NaOH titration procedure provided by Engelhard Corp. Catalysts were pretreated in-situ under flowing helium at 423 K for 5 hours. Unsupported Nafion® particles were 20~30 mesh, and could not be size reduced due to their pliable texture. Silica-supported Nafion® particles were size reduced to an average particle size less than 100 μm.

Table 1 below sets forth estimated critical properties of the alkylation reactants and the carbon dioxide co-solvent/diluent.

TABLE 1

| System (%, molar basis) | $T_C$ (K) | $P_C$ (bar) |
|---|---|---|
| i-$C_4$ (83), $C_4^=$ (17) | 408 | 36 |
| $CO_2$ (70), i-$C_4$ (25), $C_4^=$ (5) | 340 | 74 |
| $CO_2$ (73), i-$C_4$ (21), 2,2,4-TMP (5) | 353 | 91 |

The isobutane and 1-butene feeds (Matheson, 99+%) were pre-mixed to a specified I/O ratio, analyzed offline, and then transferred to an ISCO LC5000 syringe pump. During experiments, the hydrocarbon feed was pretreated online with a 6 g neutral alumina (Fisher Scientific) trap to remove any organic peroxides, which are known to be prolific coke-precursors and can contribute to catalyst deactivation (Clark, M., et al., *AIChE J.*, 45 (1999) 1559). Carbon dioxide (Airgas, 99+%) was pumped using a cooled ISCO LC5000 syringe pump. The $CO_2$ stream was pretreated online with 6 g anhydrous sodium sulfate (Fisher) to remove moisture, and 6 g neutral alumina.

Reaction pressure was maintained with a dome-loaded back-pressure regulator (Circle Seal Controls). All heated zones were controlled and monitored with a Camile 2500 data acquisition system (Camile Products). Products were analyzed online by gas chromatography with an HP 5890 II GC, equipped with an FID, and a DB-Petro 100 m column (J&W Scientific), operated at 35° C. for 30 min, ramped at 1.5°/min to 100° C., 5°/min to 250° C. for 15 min. An alkylate reference standard (Supelco) allowed identification of the trimethylpentanes (TMP) and dimethylhexanes (DMH). The combined mass of TMP and DMH is referred to hereafter as the "alkylate product". As discussed elsewhere (Clark, M., et al., *Ind. Eng. Chem. Res.*, 37 (1998) 1243), propane, an impurity in the isobutane feed, was used as an internal standard for butene conversion calculations. Since isomerization from 1-butene to 2-butene isomers is rapid over acidic catalysts, reported conversion is for all butene isomers to $C_5$ and higher products. Isobutylene formation was not observed under any conditions.

Reactor startup consisted of setting the final system temperature and pressure with $CO_2$ (or pure isobutane when $CO_2$ was not used) and starting the olefin feed pump (defined as zero time). Prior to shutdown, the reactor was flushed with $CO_2$ at reaction temperature and pressure until no hydrocarbons were observed in the effluent, following which the reactor was cooled and depressurized.

Figure 2:
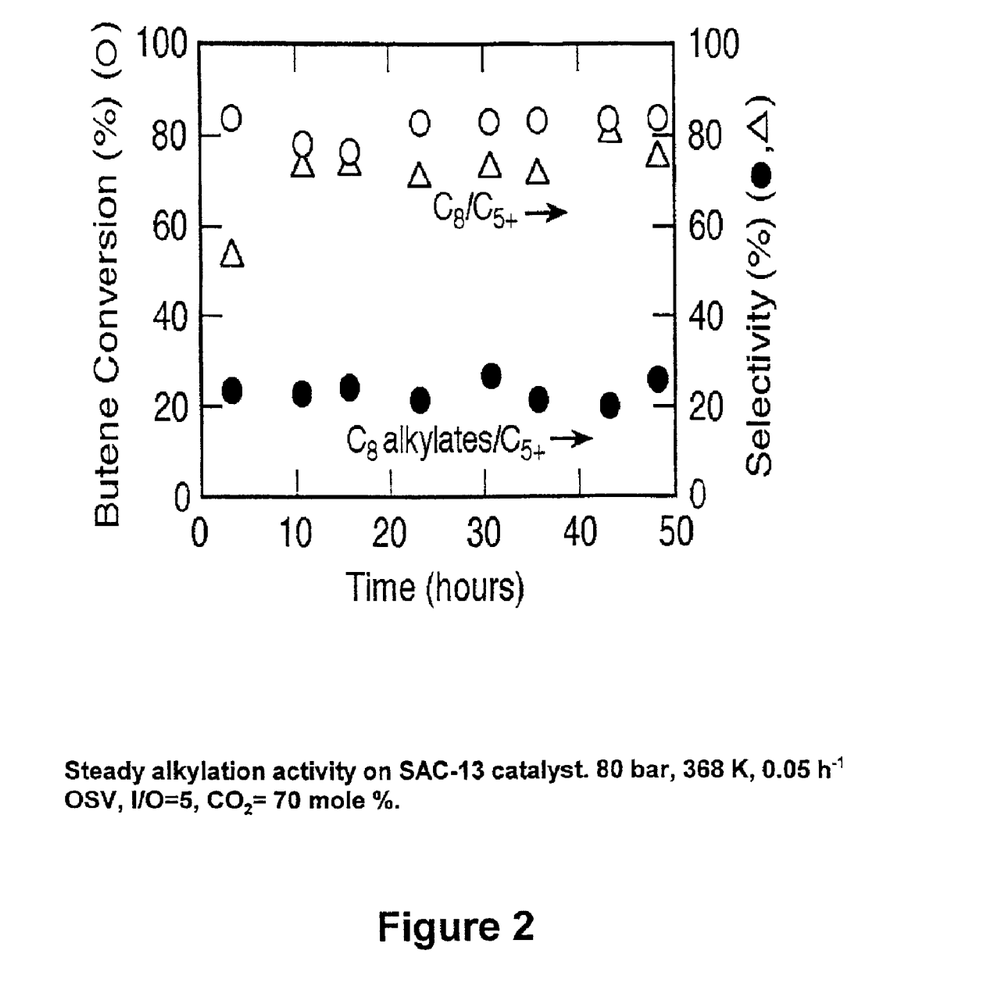
FIG. 2 is a graph illustrating butene conversion versus time in an alkylation method pursuant to the invention.

Temporal conversion and selectivity profiles obtained over a silica-supported Nafion® catalyst in a stirred reactor operated at supercritical conditions are shown in FIG. 2. The experiment was carried out at 80 bar, 368 K, and 0.05 h$^{-1}$ OWHSV, using a 5:1 isoparaffin/olefin (I/O) ratio and 2.4 fold molar excess of $CO_2$ [$(CO_2+I)/O=19$]. At these conditions, a steady butene conversion (80%) and product selectivity were demonstrated for 48 hours on stream. The alkylate selectivity (TMP+DMH) and overall $C_8$ selectivity are constant at 27% and 75% respectively. Clearly, operation in the near-supercritical region facilitates superior alkylate production over prior results using Nafion® catalysts in the liquid phase (Rørvik, T., et al. *Catal. Lett.*, 33 (1995) 127; Botella, P., et al. *J. Catal.*, 185 (1999) 371). Table 2 shows the steady state product distribution. While the $C_8$ paraffins (28 wt % of all products) are the most desired products, the large fraction of $C_8$ olefin (46%) is also a valuable product because of its high octane number.

TABLE 2

Typical Product Distribution on SAC-13 at Steady-state Conditions. 368K, 80 Bar, I/O = 5, 0.05 h$^{-1}$

| Product | % (mass) |
|---|---|
| $C_5$–$C_7$ | 15 |
| Total $C_8$'s | 74 |
|   TMP's | 11 |
|     2, 2, 4- | 5 |
|     2, 2, 3- | 4 |
|     2, 3, 4- | 2 |
|   DMH's | 17 |
|   $C_8$ olefin | 46 |
| $C_9$+ | 11 |

EXAMPLE 2

Figure 3:
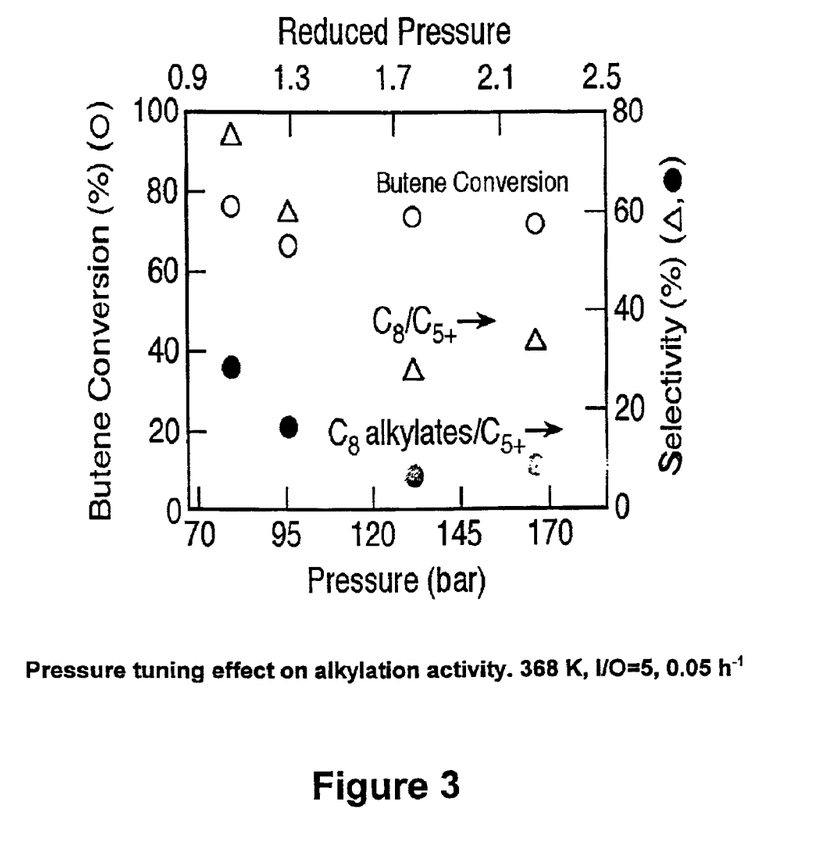
FIG. 3 is graph illustrating butene conversion versus pressure during an alkylation reaction, which demonstrates the pressure-tuning aspect of the present invention.

In order to investigate the effect of pressure-tuning on catalyst activity and product selectivity, a series of separate alkylation experiments was carried out at supercritical pressures between 80 and 167 bar. All other conditions were identical: 368 K, 0.05 h$^{-1}$, I/O=5, 2.4 fold excess $CO_2$, 1200 rpm. Each run was performed for at least 24 hours, and the steady-state averages (between 10 hours and end-of-run) for conversion and selectivity are shown in FIG. 3. The steady butene conversion (~80%) is relatively independent of pressure. At the highest supercritical pressure (167 bar), the alkylate selectivity is lowest at 7%, and the overall $C_8$ selectivity is approximately 30%. As the pressure is decreased towards the critical pressure, the observed alkylate selectivity increases nearly fourfold. The results are interpreted as follows: at near-supercritical pressures, heavier compounds ($C_{12+}$) are preferentially retained in the macropores. This in situ separation enhances the $C_8$ selectivity observed in the effluent. At higher pressures, the $C_{12+}$ compounds are solubilized more effectively by the reaction mixture and therefore less are retained in the pores, adversely affecting $C_8$ selectivity in the effluent. Below 80 bar (i.e. sub-critical pressures), the alkylate production did not reach a steady value, but gradually decreased with time. The deactivation is attributed to substantial product condensation in the catalyst pores at subcritical pressures.

The characteristics of the fresh catalysts are shown in Table 3. The 13% Nafion®/silica-supported SAC-13 has the advantage of a surface area several orders of magnitude greater than the unsupported polymer, thereby better exposing the acid sites for reaction. In the presence of compressed $CO_2$, the polymeric form of Nafion® suffered from swelling and sticking, demonstrating another advantage to the silica-supported form. Post run surface area and pore volume measurements gave roughly 70% and 90% of fresh values respectively, and did not display a systematic trend at various conditions—even in liquid phase operation. This is in contrast to the results obtained on Y zeolite (Clark, M., et al., *Ind. Eng. Chem. Res.*, 37 (1998) 1243), which showed a greater loss in surface area for a liquid phase than for a near-critical $CO_2$ phase. The very small pore sizes in Y zeolite (~13 Å) are more susceptible to pore blocking than the silica support (~95 Å). The titration of Nafion® and SAC-13 catalysts' acid sites after use showed generally 90% of fresh values, again with no systematic trend.

TABLE 3

Acidity, Surface Area (SA) and Pore Volume (PV) of Fresh Catalysts

| Catalyst | Acidity (meq/g) | SA (m$^2$/g) | PV (cm$^3$/g) |
|---|---|---|---|
| Unsupported Nafion | 0.793 | ~0.01 | n/a |
| $SiO_2$ supported Nafion (SAC-13) | 0.015 | 220 | 0.508 |

Figure 4:
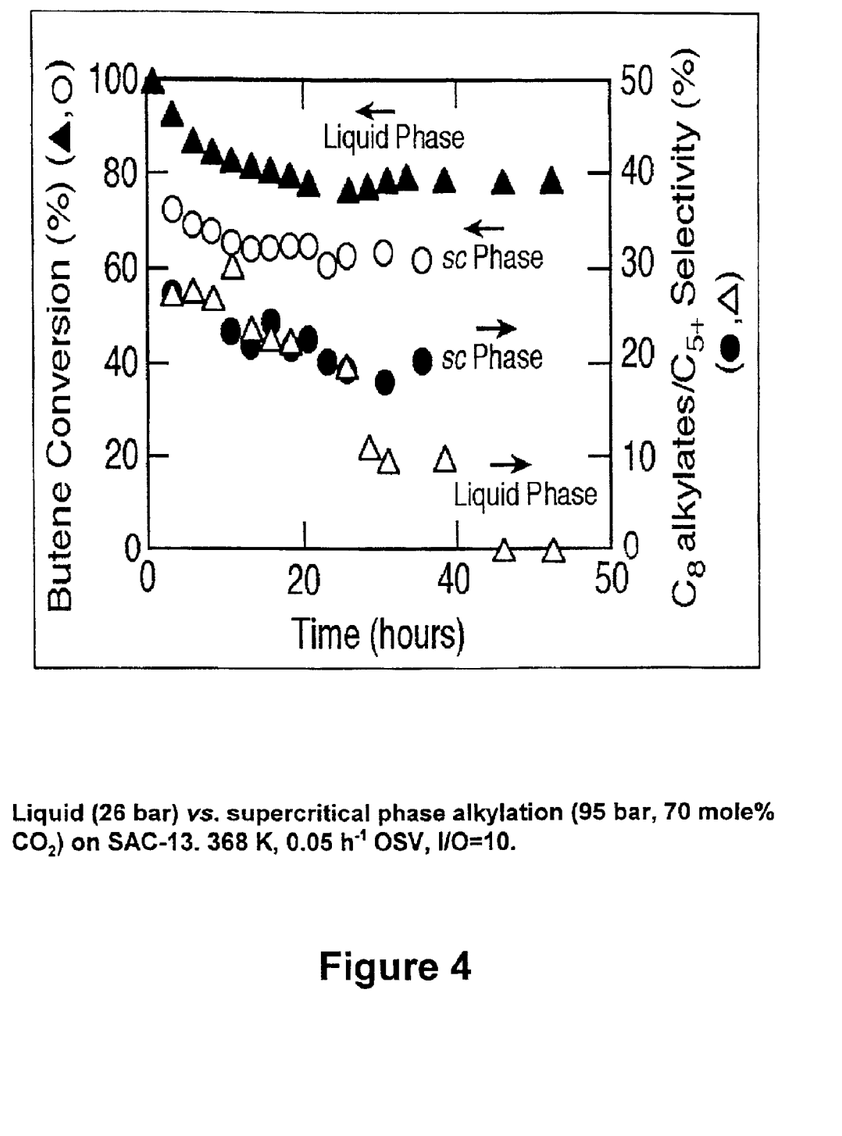
FIG. 4 is a graph illustrating butene conversion versus time using silica-supported Nafion solid catalyst in both liquid and supercritical phases.

FIG. 4 shows the butene conversion over the silica-supported Nafion® catalyst in both liquid and supercritical phases at 368 K, an OWHSV of 0.05 h$^{-1}$ and an I/O ratio of 10. The liquid phase was maintained at a pressure of 26 bar, while the supercritical phase was maintained at 95 bar, with a 2.4 fold molar excess of carbon dioxide (~70% total mole fraction $CO_2$). In both cases, a high steady butene conversion is observed. However, the alkylate selectivity continuously declines to zero after 45 hours on stream, at which point the catalyst is only active for butene oligomerization. At the supercritical condition, the acid sites responsible for alkylation are kept active, extending the production of the desired trimethylpentanes. Similar results comparing liquid and supercritical phase runs were also seen on unsupported Nafion®.

Figure 5:
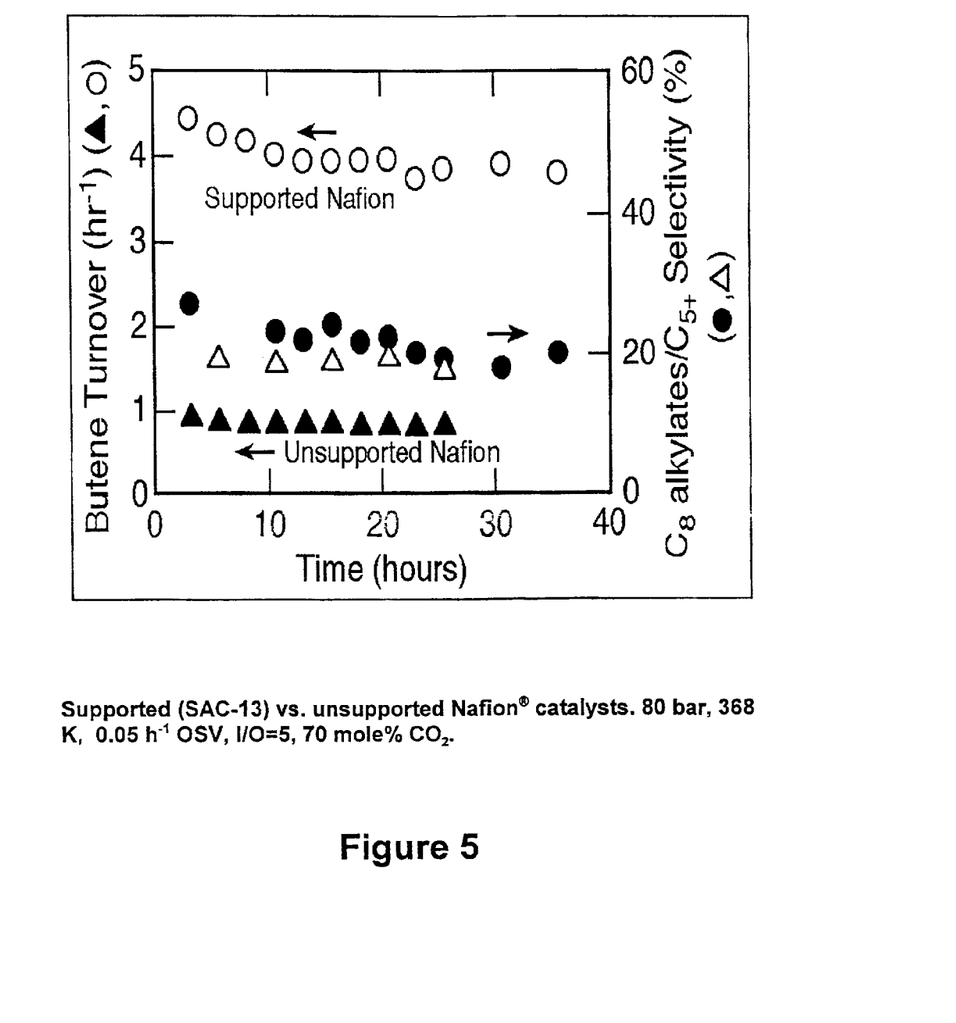
FIG. 5 is a graph illustrating butene turnover versus time in alkylation reactions using supported and unsupported catalysts, respectively.

FIG. 5 compares the activity of the silica-supported SAC-13 with unsupported Nafion® particles. Both catalysts show similar product selectivity at identical conditions. The butene turnover frequency, defined as the butene conversion rate per acid site, is enhanced fourfold when using the supported catalyst. Similar enhancements on supported Nafion® have been reported for other reactions as well (Harmer, M., et al. *Chem. Comm.*, (1997) 1803; Sun, Q., et al. *Ind. Eng. Chem. Res.*, 36 (1997) 5541; and Pálinkó, I., et al. *App. Catal. A*. 174 (1998) 147. Since hydrated Nafion® can conduct protons, acid sites that are hidden within the polymer may not be available for reaction, but may still be measured by the aqueous titration method.

The effect of temperature was examined over the range of 358 K to 378 K, keeping all other conditions constant. Only mild effects in conversion and selectivity were observed, as seen in Table 4. Increasing temperatures tend to favor the oligomerization of butene and the cracking of heavy compounds, as evidenced by a declining $C_8$ selectivity. The net result is that the alkylate yield is not significantly affected over this temperature range.

TABLE 4

Temperature Effect on Butene Conversion and Alkylate Selectively Over SAC-13. 80 bar, 0.05 h$^{-1}$, I/O = 5, 70 mole % $CO_2$

| Temperature (K) | Butene Conversion (%) | Alkylate/ $C_5$ + (%) | $C_8$/ $C_5$ + (%) |
|---|---|---|---|
| 358 | 70 | 24 | 79 |
| 368 | 77 | 28 | 76 |
| 378 | 78 | 27 | 64 |

An alternate startup procedure was also tested. Since $CO_2$ at 80 bar and 95° C. is less dense than the final reaction mixture, initial catalyst deactivation could possibly have occurred during this startup period. To address this possibility, instead of initially charging the reactor with only carbon dioxide, a 70/30 mixture of $CO_2$/isobutane was added, followed by establishing the final temperature and pressure before adding the olefin. The results showed no dependence on the startup procedure.

Figure 6:
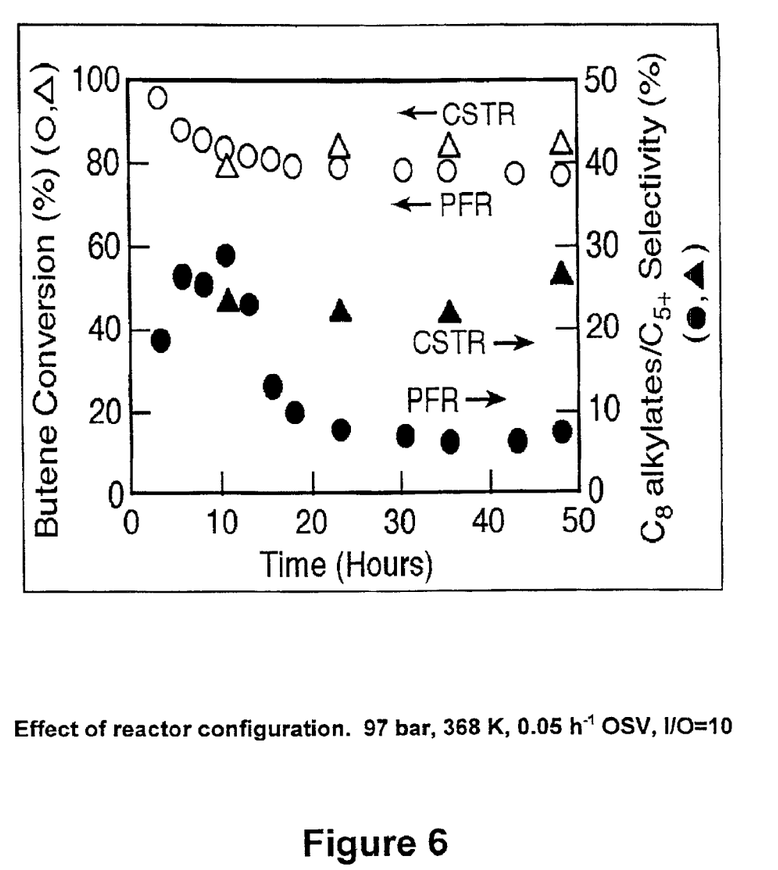
FIG. 6 is a graph illustrating butene conversion versus time in alkylation reactions using different reactor configurations.

The dimerization of butene is expected to be a second order process while alkylation would be a pseudo-first order rate process. By this rationale, a CSTR should provide enhanced alkylation activity compared to a PFR. As seen in FIG. 6, CSTR operation gives a steady alkylate selectivity, as already described, whereas the PFR shows a different steady state with lower alkylate selectivity, favoring higher molecular weight compounds in the product.

EXAMPLE 3

In this example a multiple-cycle alkylation experiment was performed, with successive alkylation and catalyst regeneration cycles.

10 g of silica-supported Nafion® acid catalyst (SAC-13, provided by Engelhard Corp.) was loaded into the reactor, and pretreated in dry nitrogen at 423 K and atmospheric pressure for 6 hours.

The reactor was a 50 mL stirred vessel (Autoclave Engineers) with an electrical heating jacket controlled by a CAMILE data acquisition and control system. The catalyst particles, between 62 and 105 μm, were suspended in the fluid by intense stirring at 1200 RPM. The reactor was purged and pressurized with carbon dioxide at 368 K and 87 bar. The isobutane/1-butene mixture was premixed to a molar ratio of 5:1, and pumped from an ISCO syringe pump. This feed was pumped at 5.4 mL/hr through a 6 g bed of neutral alumina, to adsorb any organic peroxides (which are known to be prolific coke precursors). Carbon dioxide was pumped at 6.6 mL/hr from an ISCO syringe pump (cooled to 280 K), and was passed through a bed of 6 g alumina and 6 g sodium sulfate, to adsorb any moisture in the $CO_2$ stream. The combined feed stream was fed to the bottom of the reactor. Pressure control in the reactor was maintained by a dome-loaded back-pressure regulator. The effluent stream was fitted with 5 mm and 0.5 mm filters to prevent particulates from entering the back-pressure regulator. The effluent was maintained at reaction temperature until after the pressure regulator to keep the mixture in a supercritical state. Past the back-pressure regulator, the atmospheric pressure gas was maintained at 473 K and is sampled in a HP 5890 II gas chromatograph equipped with a flame ionization detector and a DB Petro 100 m capillary column (J&W Scientific).

Figure 7:
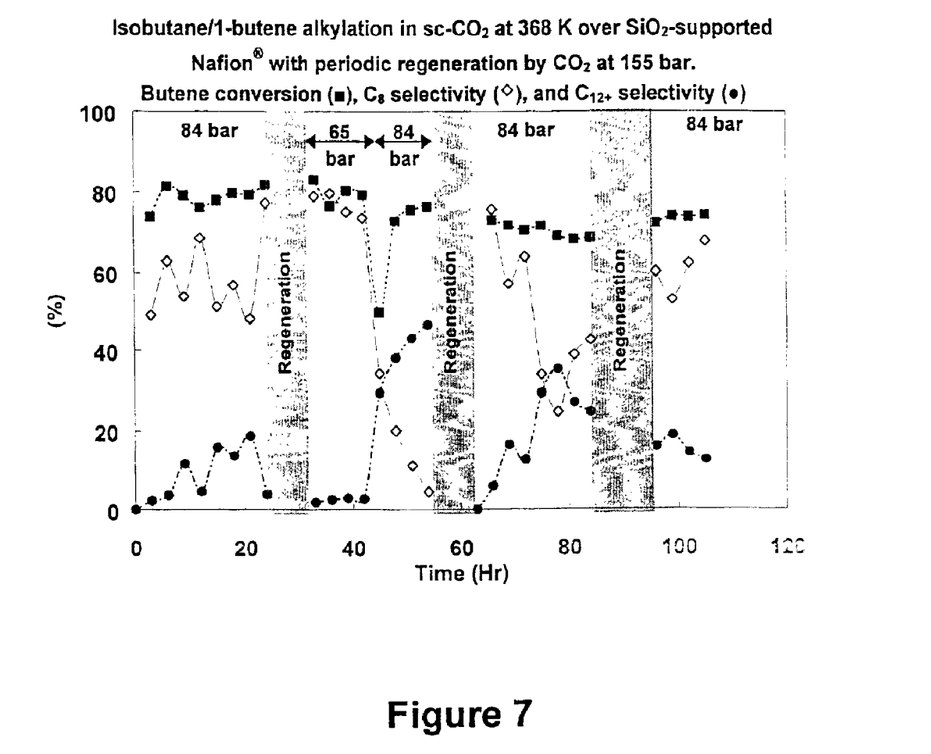
FIG. 7 is a graph illustrating butene conversion, $C_8$ selectivity and $C_{12+}$ selectivity versus time for an alkylation reaction including periodic catalyst regeneration steps.

The combined feed was passed through the reactor for 30 hours at 368 K and 87 bar. After this time, the catalyst regeneration step was started. The hydrocarbon feed was stopped, and the carbon dioxide feed was increased to 1 mL/min. The pressure was increased to 140 bar. Carbon dioxide was allowed to clean the catalyst pores for 9 hours. The pressure was returned to 87 bar and the original feed flow rates were established for the next cycle. FIG. 7 illustrates the results of this test and confirms that after each regeneration step the catalyst retained a substantial fraction of its activity, as compared with the first reaction cycle activity (usually at least about 85%).

EXAMPLE 4

In this example, an isobutane/1-butene alkylation reaction in $CO_2$ was carried out under supercritical conditions, using the preferred solid Nafion® catalyst. The results of this test are set forth in FIG. 8, a graph of % conversion of butene, $C_8$ selectivity and $C_{12+}$ selectivity over time. The reaction conditions were 368K, 78 bar, other conditions as set forth in Example 1.

Figure 8:
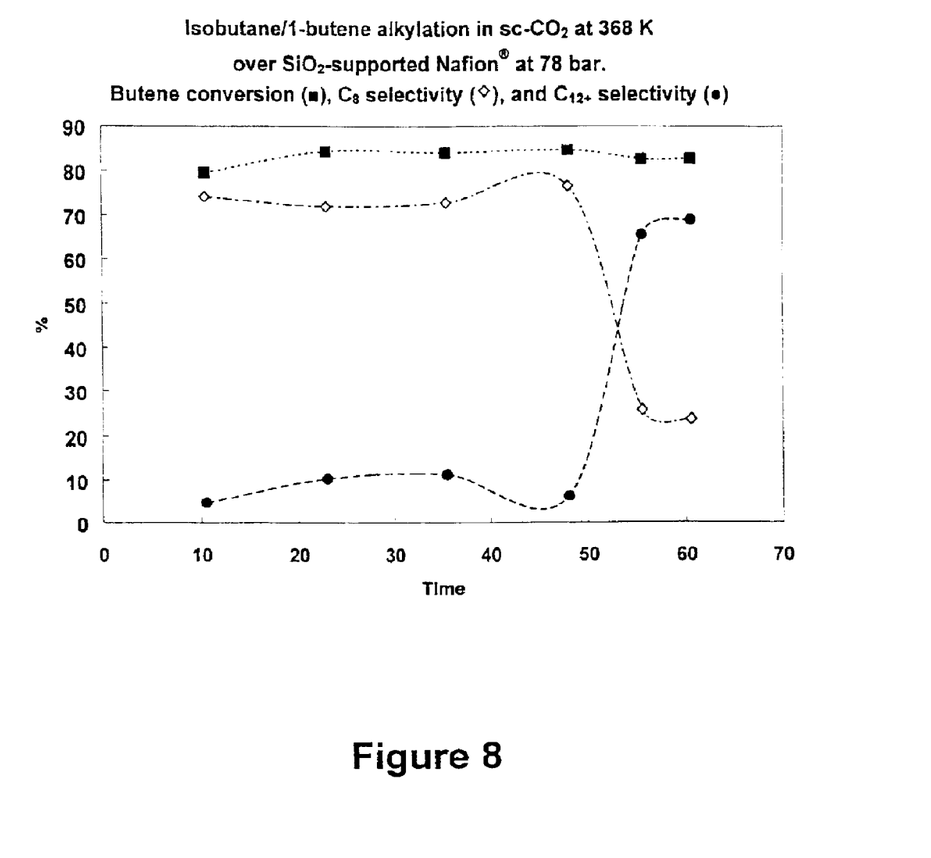
FIG. 8 is a graph illustrating butene conversion, $C_8$ selectivity and $C_{12+}$ selectivity versus time in an alkylation reaction, which demonstrates a significant decrease in $C_8$ selectivity after approximately 50 hours of reaction run time.

As shown, there is a "breakthrough" of high molecular weight compounds with increasing reaction time. At the specified operating conditions, the breakthrough typically occurs at 35–50 hours reaction time. Note the dramatic drop in selectivity of the desired $C_8$ products, and the corresponding rise in production of undesired $C_{12+}$ compounds, while butene conversion is relatively unaffected. As discussed in Example 5, it is possible to periodically clean the pores (before $C_8$ selectivity decline occurs) by dissolving the retained heavier compounds with high-pressure $CO_2$.

EXAMPLE 5

In this example, this effect of pressure-tuning on final productivity in an alkylation reaction was investigated.

The experiment was conducted as described in Example 3, with the isobutane/1-butene alkylation carried out under supercritical conditions (368K, variable pressure). The reactor pressure was maintained at 83 bar for 22 hours, and at 137 bar thereafter.

Figure 9:
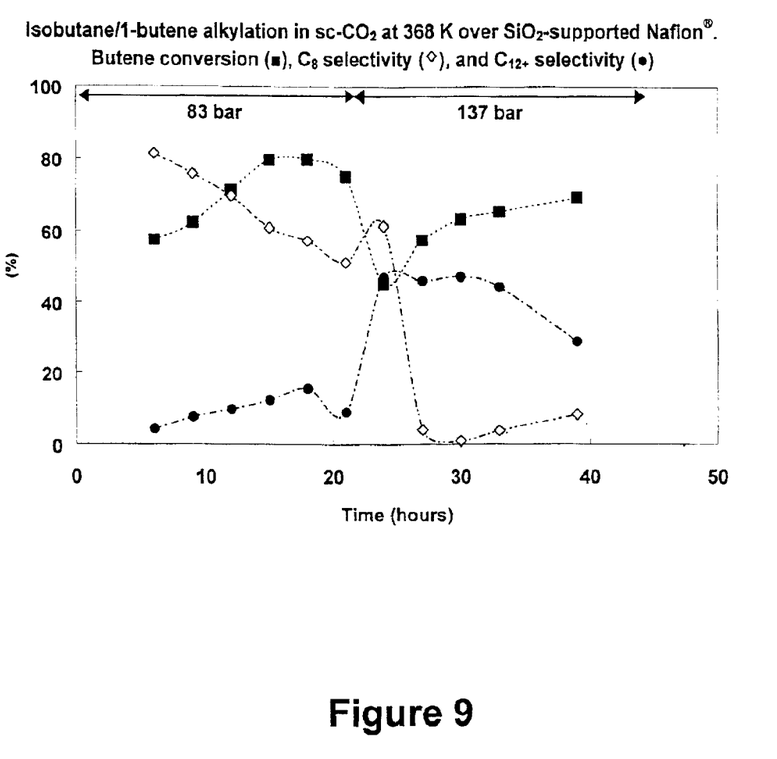
FIG. 9 is a graph illustrating butene conversion, $C_8$ selectivity and $C_{12+}$ selectivity versus time in a pressure-tuned alkylation reaction, demonstrating a significant shift in product selectivity owing to pressure-tuning.

The results of this test are plotted in FIG. 9, demonstrating the dramatic shift in selectivity which occurs when the pressure is increased, causing increased solubility of higher molecular weight products. Here, the feed flow rates are unchanged—only the reactor pressure is changed at 22 hours. A mass balance indicates that at the time of the pressure change, more hydrocarbons are leaving the reactor than are being fed. This suggests the heavy products were being "stored" inside the reactor prior to the pressure change.

Figure 10:
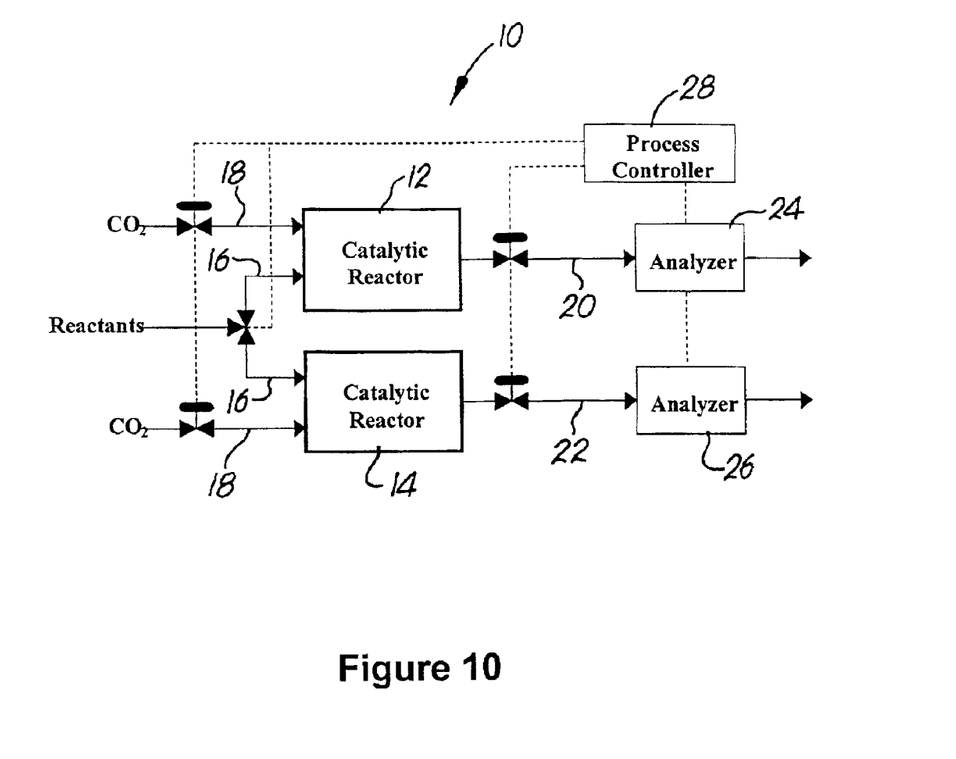
FIG. 10 is a schematic representation of a parallel alkylation reactor system permitting automated, alternate reaction and catalyst regeneration.

As indicated previously, the pressure-tuning aspects of the present invention permit relatively long runs while avoiding significant product selectivity degradation. FIG. 10 schematically depicts an automated apparatus to achieve this end. The apparatus 10 includes first and second catalytic reactors 14 each having valve-controlled reactant and co-solvent or diluent inputs 16 and 18, respectively. The output lines 20, 22 from the reactors 12, 14 are also valve-controlled and pass through appropriate analyzers 24,26 (typically gas chromatographs) designed to analyze product outputs. A process controller 28, usually in the form of a microprocessor is operably coupled with the input and output lines to the reactors 12, 14, as well as the analyzers 24, 26 as shown.

In practice, during the time that reactor 12 is being used for the desired heterogeneous reaction, the reactor 14 will be undergoing a catalyst purge/reactivation cycle. When the latter is completed, the controller 28 will then reverse the reactors, so that the catalyst within reactor 12 is treated and the desired chemical reaction is carried out in reactor 14. Generally speaking, a system of this type can readily be employed, once the breakthrough time for the reaction in question is determined, as explained in Example 4 and FIG. 8.

What is claimed is:

1. In a method of conducting a heterogeneous chemical reaction including the steps of forming a reactant mixture comprising one or more heterogeneous reactant(s) in a reactor, and causing said reactant(s) to react in the presence of a solid catalyst to yield a reaction mixture comprising said reactants and the reaction products of the reaction, the improvement which comprises using as said solid catalyst a macroporous solid catalyst having a surface area of from about 50–400 m$_2$/g, and an average pore size of from about 70–150 Å, and carrying out said reaction under conditions comprising a temperature of from about 0.9–1.3 $T_c$ of the reactant mixture and a pressure of from about 0.9–2.5 $P_c$ of the reactant mixture, said reactant mixture being formed by continuously introducing said reactant(s) into said reactor including a co-solvent or diluent under substantially steady state reactor conditions, said catalyst being susceptible to deactivation owing to coke laydown during the course of said reaction, said method including the step of regenerating said catalyst by terminating said introduction of at least one of said reactant(s) prior to a time when said solid catalyst is significantly deactivated owing to coke laydown, elevating the pressure and/or lowering the temperature within said reactor to remove at least a portion of any coke on the catalyst, resuming introduction of said reactant(s) into said reactor and reestablishing said substantially steady state conditions.

2. The method of claim 1, said surface area being about 200 m$^2$/g.

3. The method of claim 1, said catalyst comprising a perfluorinated polymer having sulfonic acid groups coupled thereto.

4. The method of claim 1, said chemical reaction selected from the group consisting of alkylation, acylation, isomerization, aromatic disproportionation, alcohol synthesis and Fischer-Tropsch reactions.

5. The method of claim 1, said temperature being from about 1.01–1.2 $T_c$ of the reactant mixture.

6. The method of claim 1, said reaction being carried out at a pressure of from about 1.01–1.2 $P_c$ of the reactant mixture.

7. The method of claim 1, the pressure within said reactor being elevated by at least about 40%, as compared with the pressure within the reactor during said chemical reaction.

8. The method of claim 1, the reactor temperature being lowered while still maintaining the reactor temperature above the $T_c$ of the co-solvent or diluent.

9. A method of conducting a heterogeneous chemical reaction comprising the steps of:

introducing one or more heterogeneous reactant(s) and a co-solvent or diluent into a reactor to form a reactant mixture comprising said reactants and the reaction products of the reaction, and causing said reactant(s) to react therein to yield a reaction mixture in the presence of a solid catalyst susceptible to deactivation owing to coke laydown during the course of said reaction, said reaction being carried out under substantially steady state near- or supercritical reaction conditions for the reactant mixture, said near- or supercritical reaction conditions comprising a temperature of from about 0.9–1.3 $T_c$ of the reactant mixture and a pressure of from about 0.9–2.5 $P_c$ of the reactant mixture;

regenerating said catalyst of coke during the course of said reaction, including the steps of interrupting said chemical reaction by terminating said introduction of at least one of said reactant(s) into said reactor prior to a time when the catalyst is significantly deactivated, and regenerating said catalyst by elevating the pressure within said reactor and/or lowering the reactor temperature to effect at least partial removal of coke from said catalyst; and resuming said chemical reaction by again introducing said reactant(s) into the reactor, and reestablishing said substantially steady state conditions.

10. The method of claim 9, said regenerating step being carried out before the rate of production of a desired reaction product falls by a factor of 20%, as compared with the steady state reaction product production rate prior to the regenerating step.

11. The method of claim 9, said solid catalyst having a surface area of from about 50–400 m$^2$/g.

12. The method of claim 9, said catalyst comprising a perfluorinated polymer having sulfonic acid groups coupled thereto.

13. The method of claim 9, said chemical reaction selected from the group consisting of alkylation, acylation, isomerization, aromatic disproportionation, alcohol synthesis and Fischer-Tropsch reactions.

14. The method of claim 9, said temperature being from about 1.01–1.2 $T_c$ of the reactant mixture.

15. The method of claim 9, said reaction being carried out at a pressure of from about 1.01–1.2 $P_c$ of the reactant mixture.

16. The method of claim 9, the pressure within said reactor during said regenerating step being elevated by at least about 40%, as compared with the pressure within the reactor during said chemical reaction.

17. The method of claim 9, the reactor temperature being lowered while still maintaining the reactor temperature above the $T_c$ of the co-solvent or diluent.

18. The method of claim 9, including the step of recovering said removed coke.

19. A method of conducting a heterogeneous chemical reaction comprising the steps of:

introducing one or more heterogeneous reactant(s) and a co-solvent or diluent into a reactor to form a reactant mixture, and causing said reactant(s) to react therein to yield a reaction mixture in the presence of a solid catalyst susceptible to deactivation owing to coke laydown during the course of said reaction, said reaction being carried out under substantially steady state near- or supereritical reaction conditions for the reactant mixture, said near- or supercritical reaction conditions comprising a temperature of from about 0.9–1.3 $T_c$ of the reactant mixture and a pressure of from about 0.9–2.5 $P_c$ of the reactant mixture;

regenerating said catalyst of coke during the course of said reaction, including the steps of interrupting said chemical reaction by terminating said introduction of at least one of said reactant(s) into said reactor prior to a time when the catalyst is significantly deactivated, and regenerating said catalyst by lowering the reactor temperature to effect at least partial removal of coke from said catalyst; and resuming said chemical reaction by again introducing said reactant(s) into the reactor, and reestablishing said substantially steady state conditions.

20. A method of conducting a heterogeneous alkylation reaction, said reaction including isoparaffin, an olefin, and a molar excess of an inert co-solvent or diluent as reactants, said method comprising the steps of:

introducing one or more heterogeneous reactant(s) and a co-solvent or diluent into a reactor to form a reactant mixture, and causing said reactant(s) to react therein to yield a reaction mixture in the presence of a solid catalyst susceptible to deactivation owing to coke lay-down during the course of said reaction, said reaction being carried out under substantially steady state near- or supercritical reaction conditions for the reactant mixture, said near- or supercritical reaction conditions comprising a temperature of from about $0.9-1.3$ $T_c$ of the reactant mixture and a pressure of from about $0.9-2.5$ $P_c$ of the reactant mixture;

regenerating said catalyst of coke during the course of said reaction, including the steps of interrupting said chemical reaction by terminating said introduction of at least one of said reactant(s) into said reactor prior to a time when the catalyst is significantly deactivated, and regenerating said catalyst by elevating the pressure within said reactor and/or lowering the reactor temperature to effect at least partial removal of coke from said catalyst; and resuming said chemical reaction by again introducing said reactant(s) into the reactor, and reestablishing said substantially steady state conditions.

21. A method of conducting a heterogeneous chemical reaction comprising the steps of:

introducing one or more heterogeneous reactant(s) and a co-solvent or diluent into a reactor to form a reactant mixture, and causing said reactant(s) to react therein to yield a reaction mixture in the presence of a solid catalyst susceptible to deactivation owing to coke lay-down during the course of said reaction, said reaction being carried out under substantially steady state near- or supereritical reaction conditions for the reactant mixture, said near- or supercritical reaction conditions comprising a temperature of from about $0.9-1.3$ $T_c$ of the reactant mixture and a pressure of from about $0.9-2.5$ $P_c$ of the reactant mixture;

regenerating said catalyst of coke during the course of said reaction, including the steps of interrupting said chemical reaction by terminating said introduction of at least one of said reactant(s) into said reactor prior to a time when the catalyst is significantly deactivated, and regenerating said catalyst by increasing the density of said reaction mixture to effect at least partial removal of coke from said catalyst; and resuming said chemical reaction by again introducing said reactant(s) into the reactor, and reestablishing said substantially steady state conditions.

* * * * *